US00PP18380P2

(12) United States Plant Patent
Olsthoorn

(10) Patent No.: US PP18,380 P2
(45) Date of Patent: Jan. 1, 2008

(54) ***SPATHIPHYLLUM* PLANT NAMED 'SWEET SILVIO'**

(50) Latin Name: *Spathiphyllum Schott*
Varietal Denomination: Sweet Silvio

(75) Inventor: Petrus C. M. Olsthoorn, Honselersdijk (NL)

(73) Assignee: P.C.M. Olsthoorn Holding BV, Honselersdijk (NL)

( * ) Notice: Subject to any disclaimer, the term of this patent is extended or adjusted under 35 U.S.C. 154(b) by 0 days.

(21) Appl. No.: 11/442,939

(22) Filed: May 30, 2006

(51) Int. Cl.
*A01H 5/00* (2006.01)

(52) U.S. Cl. ..... Plt./364

(58) Field of Classification Search ..... Plt./364
See application file for complete search history.

*Primary Examiner*—Kent Bell
*Assistant Examiner*—S. B. McCormick-Ewoldt

(57) ABSTRACT

A new cultivar of *Spathiphyllum* plant named 'Sweet Silvio' that is characterized by a good response to flower initiation treatment, consistent flower production, green leaves and white spathes.

1 Drawing Sheet

Botanical Classification: *Spathiphyllum Schott.* Variety Denomination: 'Sweet Silvio'.

BACKGROUND OF THE INVENTION

The present invention relates to a new and distinct cultivar of *Spathiphyllum* plant botanically known as *Spathiphyllum Schott.* and hereinafter referred to by the cultivar name 'Sweet Silvio'.

'Sweet Silvio' is a hybrid that originated from the hybridization of the female or seed parent a proprietary *Spathiphyllum Schott.* identified as 96341-1 (not patented) and the male or pollen parent a proprietary *Spathiphyllum Schott.* identified as 96099-50 (not patented). The cultivar 'Sweet Silvio' was selected by the inventor in September of 1999 as a single plant within the progeny of the stated cross in Honselersdijk, The Netherlands.

Asexual reproduction by tissue culture of the new cultivar 'Sweet Silvio' was first performed in 2000 in Honselersdjik, The Netherlands. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Spathiphyllum* cultivar 'Sweet Silvio'.

1. *Spathiphyllum* 'Sweet Silvio' consistently produces flowers.
2. *Spathiphyllum* 'Sweet Silvio' exhibits green leaves.
3. *Spathiphyllum* 'Sweet Silvio' exhibits white spathes.
4. *Spathiphyllum* 'Sweet Silvio' responds very well to flower initiation treatment.

The closest comparison cultivar is *Spathiphyllum* 'Sweet Pablo' (U.S. Plant Pat. No. 10,817). The new cultivar 'Sweet Silvio' is distinguishable from 'Sweet Pablo' by the following characteristics:

1. 'Sweet Silvio' produces flowers more consistently than 'Sweet Pablo'.
2. 'Sweet Silvio' has a shorter height than 'Sweet Pablo'.

3. 'Sweet Silvio' has larger leaves than those of 'Sweet Pablo'.

The new cultivar 'Sweet Silvio' is distinguishable from the male parent *Spathiphyllum* '96099-50' in having narrower leaves. The new cultivar 'Sweet Silvio' is distinguishable from the female parent *Spathiphyllum* '96341-1' in not having fragrant flowers.

BRIEF DESCRIPTION OF THE DRAWING

The accompanying photograph illustrates the distinguishing traits of *Spathiphyllum* 'Sweet Silvio'. The plant in the photograph shows an overall view of a 42 week old plant. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Spathiphyllum* cultivar named 'Sweet Silvio'. Data was collected in Honselersdijk, The Netherlands from 42 week old greenhouse grown plants in 17 cm containers. The time of year was Spring and the average temperatures was 22 degrees Centigrade during the day and 22 degrees Centigrade at night. No photoperiodic treatments were used. 80–100 PPM of Gibberallic acid was applied for flower initiation. Color determinations are in accordance with The Royal Horticultural Society Colour Chart 2001 edition, except where general color terms of ordinary dictionary significance are used. The growing requirements are similar to the species. 'Sweet Silvio' has not been tested under all possible conditions and phenotypic differences may be observed with variations in environmental, climatic, and cultural conditions, however, without any variance in genotype.

Botanical classification: *Spathiphyllum Schott.* 'Sweet Silvio'.

Use: Ornamental.

Parentage: 'Sweet Silvio' is a hybrid plant that resulted from the hybridization of the following parent plants:

*Female parent.*—A proprietary *Spathiphyllum Schott.* identified as '96341-1'.

*Male parent.*—A proprietary *Spathiphyllum Schott.* identified as '96099-50'.

Vigor: Moderate.

Growth rate: Moderate.

Growth habit: Free branching from base, bushy and dense.

Plant shape: Flattened globular with inflorescences on top.

Suitable container size: At least 2 L container.

Height: Average 48 cm to top of leaf plane, 62 cm to top of inflorescences.

Width: Average 78 cm in width.

Hardiness: USDA Zone 10.

Propagation: Tissue Culture.

Time to initiate roots (summer and winter): Approximately 14 days to produce roots on an initial cutting.

Time to produce a rooted cutting or liner (summer and winter): Approximately 39 days.

Root system: Fine and fibrous.

Stem: No stems, only short stem-like basal clumps, average 8, 144A to 144B.

Foliage:

*Texture.*—Smooth.

*Appearance.*—Glossy.

*Leaf arrangement.*—Alternate.

*Compound or single.*—Single.

*Leaf shape.*—Elliptic to narrow elliptic.

*Leaf apex.*—apiculate.

*Leaf base.*—Attenuate.

*Leaf length.*—Average 29.4 cm. in length.

*Leaf width.*—12.7 cm in width.

*Quantity of leaves per clump.*—Average 6.

*Pubescence.*—Absent.

*Leaf margin.*—Entire, slightly wavy.

*Vein pattern.*—Pinnate.

*Young leaf color* (*upper surface*).—Between 141A and 143A.

*Young leaf color* (*lower surface*).—Between 137B and 137C.

*Mature leaf color* (*upper surface*).—Between 137A and 139A.

*Mature leaf color* (*lower surface*).—137B.

*Vein color* (*lower surface*).—141A to 141B.

*Vein color* (*upper surface*).—144B.

*Leaf attachment.*—Petiolate.

*Petiole dimensions.*—Average 24.9 cm in length excluding geniculum, 4 mm in diameter below geniculum to 6 mm in diameter above clump.

*Petiole aspect.*—Round.

*Petiole color.*—Base between 144A and 144B, top between 141A and 143A.

*Geniculum dimensions.*—Average 2.9 cm in length and 4.5 mm in diameter.

*Geniculum aspect.*—Rounded, dull, glabrous.

*Geniculum color.*—143B to 143C.

*Petiole wing dimensions.*—Average 20.1 cm in length and 8 mm in diameter.

*Petiole wing color.*—Base 144A, top between 141A and 143A.

*Durability of foliage to stress.*—High.

Inflorescence:

*Inflorescence arrangement.*—Flowering structures arise close to the petioles in the centers of the clumps.

*Quantity of inflorescences per plant.*—Average 10.

*Inflorescence dimensions.*—On average 15.8 cm tall and on average 3.1 cm in depth.

*Natural flowering season.*—Autumn to spring.

*Flowering habit.*—Continuously.

*Time to flower or response time.*—Approximately 38 weeks.

*Fragrance.*—Slight.

*Self-cleaning or persistent.*—Persistent.

*Flower longevity.*—Lasts approximately 3 weeks on plant.

*Spathe aspect.*—Slightly cupped.

*Spathe dimensions.*—Average 15.8 cm in length and 7.4 cm in width.

*Spathe texture.*—Glabrous, slightly leathery.

*Spathe aspect.*—Vertically placed, tips slightly pointed backwards in an average angle of 30°.

*Spathe shape.*—Broad elliptic.

*Spathe margin.*—Entire, slightly wavy.

*Spathe apex.*—Apiculate.

*Spathe base.*—Cuneate.

*Spathe color when opening* (*front side*).—155C, main vein 143A.

*Spathe color when opening* (*back side*).—155C, main vein 143A.

*Spathe color when fully opened* (*front side*).—155C, main vein 143A.

*Spathe color when fully opened* (*back side*).—155C, main vein 143A.

*Spathe color fading to.*—Between 143A and 143C.

*Spadix shape.*—Columnar.

*Spadix aspect.*—Spadices placed vertically on top of peduncle.

*Spadix tip.*—Obtuse.

*Spadix base.*—Obtuse.

*Spadix dimensions.*—Average 5.9 cm in length and 1.6 mm in diameter.

*Spadix color when opening.*—158A to 158B.

*Spadix color when fully opened.*—158B.

*Quantity of flowers per spadix.*—Average 200.

*Spadix flower arrangement.*—Bisexual, rounded.

*Spadix flower dimensions.*—3.5 mm in diameter and 3 mm in depth.

Reproductive organs:

*Anther color.*—158D.

*Amount of pollen.*—Very high.

*Pollen color.*—155D.

*Stigma color.*—158D.

*Ovary color.*—158D.

Peduncle:

*Peduncle dimensions.*—Average 43.7 cm in length and 4.0 mm. in diameter.

*Peduncle angle.*—15° from vertical.

*Peduncle color.*—Between 137C and 138A.

*Peduncle strength.*—Strong.

Seed: Seed production has not been observed.

Disease and insect resistance: Plants of the new *Spathiphyllum* have not been observed for disease or insect resistance.

It is claimed:

1. A new and distinct variety of *Spathiphyllum* plant named 'Sweet Silvio' as described and illustrated.

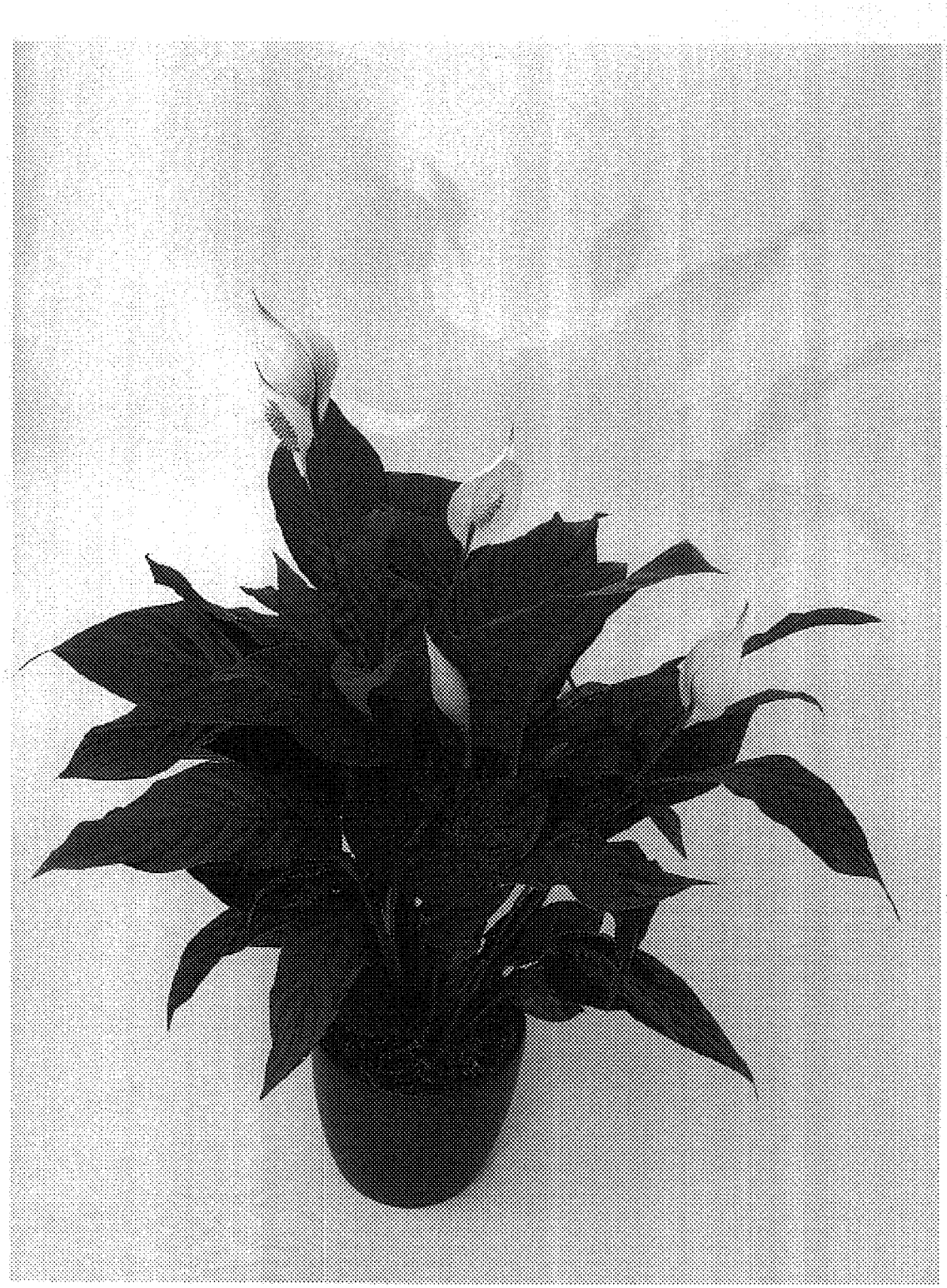

* * * * *